(12) United States Patent
Wo et al.

(10) Patent No.: US 10,596,571 B2
(45) Date of Patent: Mar. 24, 2020

(54) COLLECTION COMPONENT AND SAMPLE PROCESSING KIT HAVING THE SAME

(71) Applicant: National Taiwan University, Taipei (TW)

(72) Inventors: Andrew Man Chung Wo, Taipei (TW); Chen-Lin Chen, Taipei (TW); Cheng-Wei Yang, Taipei (TW); Wei-Fan Hsu, Taipei (TW)

(73) Assignee: National Taiwan University, Taipei (TW)

( * ) Notice: Subject to any disclaimer, the term of this patent is extended or adjusted under 35 U.S.C. 154(b) by 198 days.

(21) Appl. No.: 15/323,105

(22) PCT Filed: Jul. 2, 2015

(86) PCT No.: PCT/US2015/039087
§ 371 (c)(1),
(2) Date: Dec. 30, 2016

(87) PCT Pub. No.: WO2016/004371
PCT Pub. Date: Jan. 7, 2016

(65) Prior Publication Data
US 2018/0133714 A1    May 17, 2018

Related U.S. Application Data

(60) Provisional application No. 62/019,900, filed on Jul. 2, 2014.

(51) Int. Cl.
*B01L 99/00*    (2010.01)
*B01L 3/00*     (2006.01)
(Continued)

(52) U.S. Cl.
CPC ..... *B01L 3/502753* (2013.01); *B01L 3/50273* (2013.01); *B01L 3/502715* (2013.01); *B01L 3/567* (2013.01); *G01N 1/4077* (2013.01); *G01N 33/491* (2013.01); *G01N 35/00069* (2013.01); *B01L 2200/025* (2013.01); *B01L 2200/027* (2013.01); *B01L 2200/04* (2013.01); *B01L 2200/06* (2013.01); *B01L 2300/0803* (2013.01); *B01L 2300/0816* (2013.01); *B01L 2300/0858* (2013.01); *B01L 2300/0864* (2013.01); *B01L 2400/0409* (2013.01); *B01L 2400/0487* (2013.01); *B01L 2400/0655* (2013.01); *G01N 2001/4083* (2013.01)

(58) Field of Classification Search
CPC .................. G01N 35/00069; B01L 2300/0803
See application file for complete search history.

(56) References Cited

U.S. PATENT DOCUMENTS

| 2002/0176342 | A1* | 11/2002 | Worthington | G01N 15/1475 369/53.31 |
| 2004/0116686 | A1* | 6/2004 | Akashi | B01L 3/50273 536/25.4 |

(Continued)

*Primary Examiner* — Paul S Hyun
(74) *Attorney, Agent, or Firm* — JCIPRNET

(57) ABSTRACT

A sample processing kit including a centrifugal microfluidic component and a collection component detachably fitted into the microfluidic component is provided. Upon the application of the sample processing kit, target molecules or cells may be separated and collected by the collection component for further experimentation.

13 Claims, 18 Drawing Sheets

(51) Int. Cl.
  *G01N 35/00* (2006.01)
  *G01N 1/40* (2006.01)
  *G01N 33/49* (2006.01)

(56) References Cited

U.S. PATENT DOCUMENTS

| | | | | |
|---|---|---|---|---|
| 2004/0200724 | A1* | 10/2004 | Fujii | F04B 43/043 |
| | | | | 204/601 |
| 2007/0154895 | A1* | 7/2007 | Spaid | B01L 3/502715 |
| | | | | 435/6.19 |
| 2010/0055766 | A1* | 3/2010 | Hwang | B01L 3/502738 |
| | | | | 435/259 |
| 2011/0111987 | A1* | 5/2011 | Siegrist | B01L 3/5027 |
| | | | | 506/39 |

* cited by examiner

COLLECTION COMPONENT AND SAMPLE PROCESSING KIT HAVING THE SAME

CROSS-REFERENCE TO RELATED APPLICATION

This application is a 371 of international application of PCT application serial no. PCT/US2015/039087, filed on Jul. 2, 2015, which claims the priority benefit of U.S. provisional application No. 62/019,900, filed on Jul. 2, 2014. The entirety of each of the abovementioned patent applications is hereby incorporated by reference herein and made a part of this specification.

BACKGROUND OF THE INVENTION

1. Field of the Invention

The present invention generally relates to a sample separation and collection kit. More particularly, the present invention relates to a detachable collection component and a sample processing kit having the same.

2. Description of Related Art

Although the microfluidic technology has been widely applied in biological, medical and biochemical fields, the centrifugal microfluidic platform has generally been used as a research tool. Due to the design of non-continuous fluidic input of the sample in the centrifugal microfluidic platform, the centrifugal microfluidic devices are incongruous for the handling of samples of large volumes and unable to serve as commercial test platform or kits. In addition, better handling of the isolated or collected portion of the sample that has been processes by the centrifugal microfluidic platform is required for further experimentation.

SUMMARY OF THE INVENTION

This invention provides a sample processing kit including at least one centrifugal microfluidic disk and at least one collection component removably fitted into the centrifugal microfluidic disk. By using such sample processing kit, target molecules or cells may be separated within the centrifugal microfluidic disk by density gradient separation and collected by the collection component. Also, the sample processing kit is applicable for an automated workstation of continuous fluidic input, so that samples of large volumes can be easily processed.

The present invention is directed to a sample processing kit comprising at least one centrifugal microfluidic component and at least one collection component. The centrifugal microfluidic component includes a sample inlet for loading a biological sample, a separation chamber, a settling chamber and a fitting site for tightly fitting the collection component. The collection component is detachably fitted into the fitting site. The separation chamber is connected with the sample inlet, and the settling chamber is connected with the separation chamber. During the centrifugal process, the biological sample is processed and separated into a to-be-collected portion entering into the separation chamber and a remaining portion entering into the settling chamber. The collection component includes a chip body having an intake opening thereon and a collection chamber therein. The collection chamber with the intake opening is connected with the separation chamber of the centrifugal microfluidic disk for receiving the biological sample.

The present invention also provides a collection component, applicable for a centrifugal microfluidic disk of a sample processing kit. The collection component includes a chip body having an intake opening thereon and a collection chamber therein. The collection chamber with the intake opening is connected with a separation chamber of the centrifugal microfluidic disk. A biological sample loaded from a sample inlet of the centrifugal microfluidic disk and passing through the separation chamber of the centrifugal microfluidic disk is collected by the collection chamber of the collection component.

In order to make the above and other features and advantages of the present invention more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

Common reference numerals are used throughout the drawings and the detailed description to indicate the same elements. The present invention will be more apparent from the following detailed description taken in conjunction with the accompanying drawings.

DESCRIPTION OF THE EMBODIMENTS

The present invention is directed to a detachable collection component, removably fitted to a centrifugal microfluidic disk and a sample processing kit comprising the detachable collection component and the centrifugal microfluidic disk. The sample processing kit can be used for processing (i.e. separating, collecting and/or labeling) cells or target molecules loaded to the centrifugal microfluidic disk by using the density gradient. Also, the sample processing kit of the present invention can be operated by an automated workstation for operating the centrifugal microfluidic disk and performing the processing of the biological sample.

The sample processing kit disclosed in the present invention may be applied to process various types of samples, including the whole blood sample, the plasma fluids, urine or other body or biological fluids.

Figure 1A:
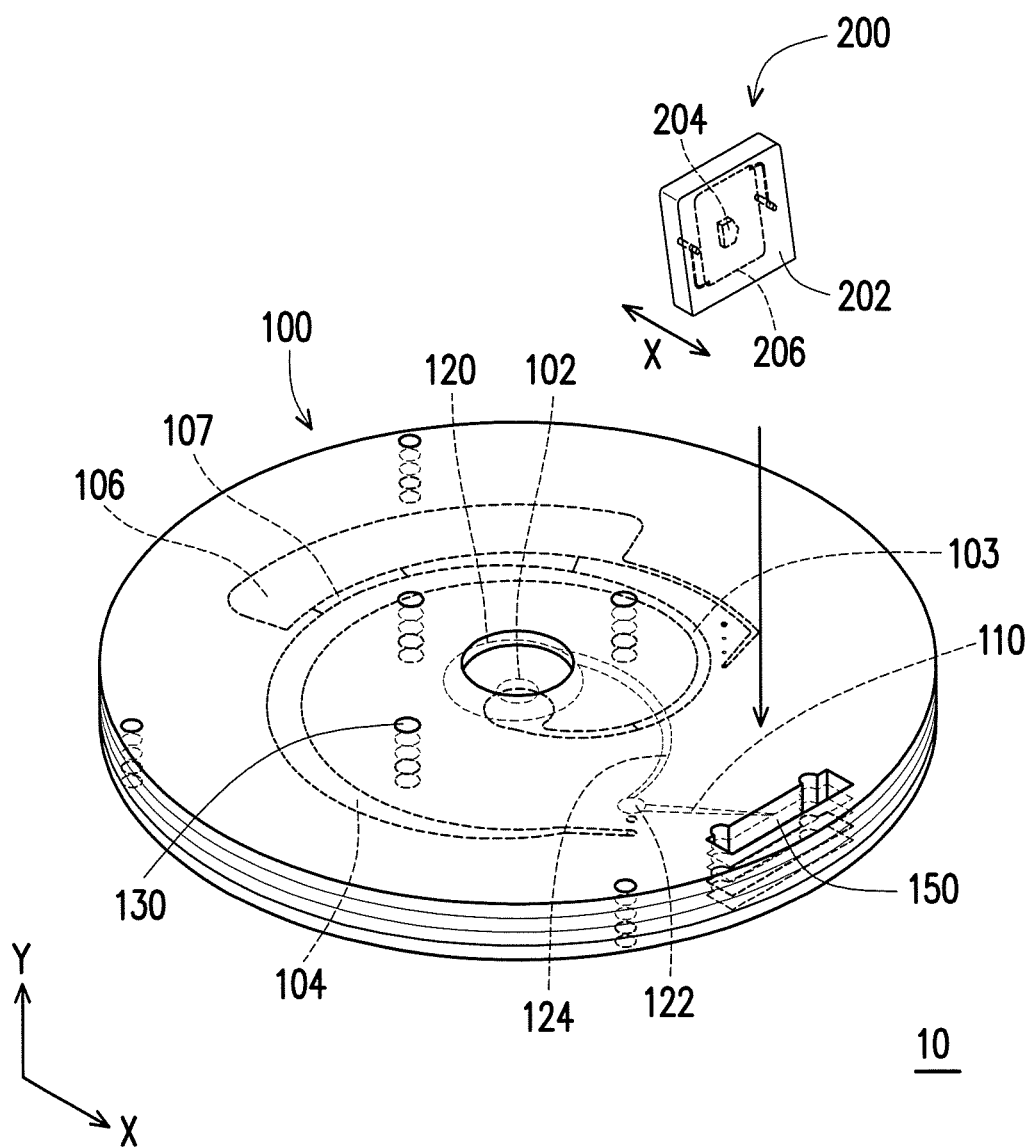
FIG. 1A schematically illustrates a three-dimensional view of a sample processing kit according to an embodiment of this invention.
Figure 1B:
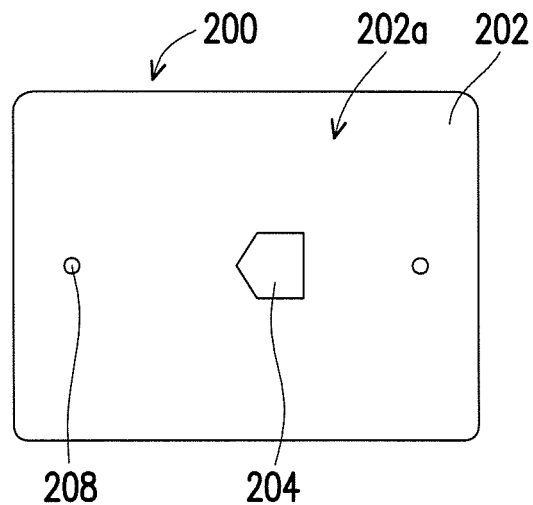
FIG. 1B shows a top view of the collection component of the sample processing kit of FIG. 1A.
Figure 1C:
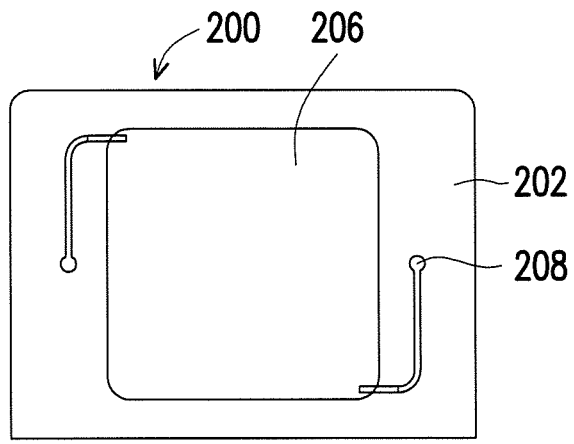
FIG. 1C schematically illustrates a cross-sectional view of the collection component of the sample processing kit of FIG. 1A.

FIG. 1A schematically illustrates a three-dimensional view of a sample processing kit according to an embodiment of this invention. FIG. 1B shows a top view of the collection component of the sample processing kit of FIG. 1A, while FIG. 1C schematically illustrates a cross-sectional view of the collection component of the sample processing kit of FIG. 1A. The cross-section of FIG. 1C is taken transversely to the thickness direction of the collection component in FIG. 1A.

Referring to FIG. 1A, the sample processing kit 10 includes at least a centrifugal microfluidic disk 100 and a collection component 200. The collection component 200 is removable and detachable and can be fitted or vertically inserted into a slot 150 of the centrifugal microfluidic disk 100. The fitted collection component 200 stands upright to the microfluidic disk 100. That is, after being fitted to the disk, a thickness direction X of the collection component 200 is substantially vertical or perpendicular to a thickness direction Y of the microfluidic disk 100. The centrifugal microfluidic disk 100 may be a round or elliptical disk and the microfluidic disk 100 may be fabricated as several slices and then assembled or stacked together. The material of the microfluidic disk 100 may be a plastic material, such as polymethyl methacrylate (PMMA), or other thermoplastics. The diameter of the microfluidic disk 100 may ranges from 6 to 18 centimeters, preferably 12-14 centimeters, for example. The microfluidic disk 100 includes more than one shaft holes 130 for accommodating the shaft of spinning. Although the centrifugal microfluidic disk is named as a "disk", it is in fact a centrifugal microfluidic processing component, and the term "disk" is not intended to limit the shape or the outline design of the component.

Referring to FIG. 1A, the microfluidic disk 100 at least includes a sample inlet 102, a separation chamber 104 and a settling chamber 106. The sample inlet 102 is located on a central position of the disk 100 and the sample may be loaded into the disk 100 through the sample inlet 102. The separation chamber 104 is connected with the sample inlet 102 through a connecting channel 103. The connecting channel 103 and the separation chamber 104 are jointly designed to be a spiral shape spiraling outward from the central sample inlet 102. The separation chamber 104 has an arc shape and the arc-shape portion (the portion substantially along the circumferential edge of the disk) of the separation chamber 104 has a length of about 2-20 centimeters and a width of about 0.1-2 centimeters.

The connecting channel 103 (the portion connected to the sample inlet to the circumferential portion) has a dimension of about 0.1-1 centimeter.

The settling chamber 106 is arranged surrounding the separation chamber 104 but is separate from the separation chamber 104 with a distance in-between. The settling chamber 106 is connected with the separation chamber 104 through a connecting portion 107 located in-between, so that the injected fluid can flow between the separation chamber 104 and the settling chamber 106. One end of the connecting channel 103 is physically connected to the sample inlet 102, while one end 104b of the separation chamber 104 is physically connected to a junction 122. The microfluidic disk 100 also includes the slot 150 located at a peripheral portion of the microfluidic disk 100. The slot 150 is configured to accommodate the detachable collection component 200. That is, the shape of the slot 150 should be designed to tightly fit with the collection component 200.

In principle, the slot can be considered as a fitting site and the collection component is fitted to the fitting site through the tight-fitting mechanism.

As shown in FIG. 1A, the disk 100 also includes a chemical inlet or reagent inlet 120 at the central position of the disk 100 and reaction reagents may be loaded into the disk 100 via the reagent inlet 120. The reagent inlet 120 and the sample inlet 102 are both round openings, but the reagent inlet 120 and the sample inlet 102 are of different sizes, are located at different levels and arranged in a concentric way. The reagent inlet 120 located at the upper level has a size larger than the size of the sample inlet 102 located at the lower level. The reagent inlet 120 is connected with the junction 122 through a linking channel 124. The separated sample or reagent flowing through the junction 122 further flows into the collection component 200 fitted within the slot 150 through a conveying channel 110. The end of the conveying channel 110 functions as an outlet of the separated sample or the reagent. The junction 122 extends vertically and communicates with the conveying channel 110 located at the upper level and the separation chamber 104 located at the lower level. The separated sample can flow from the end 104b of the separation chamber 104 into the collection component 200 fitted within the slot 150, through the junction 122 and the conveying channel 110. The flow path of the reagent loaded from the chemical inlet 120 is located at a different level and along a different route from the flow path of the sample loaded from the sample inlet. The collection component 200 may be removed from the disk in the later stage.

Referring to FIGS. 1B-1C, the collection component 200 includes a chip body 202 having an intake opening 204 on the top surface 202a. The intake opening 204 opens into a collection chamber 206 within the chip body 202. As shown in FIG. 1C, the collection chamber 206 is connected with at least one waste outlet 208 (two outlets are shown herein) so that the extra or needless fluid or running solution is discharged from the waste outlet 208. The intake opening 204 in fact functions as an inlet for receiving the sample flowing from the separation chamber 104 via the junction 122 and the conveying channel 110. As shown in FIG. 1A, when the collection component 200 is inserted into the microfluidic disk 100, the intake opening 204 faces toward the end of the conveying channel 110 of the disk 100, so as to receive the separated sample or other fluid.

Figure 1D:
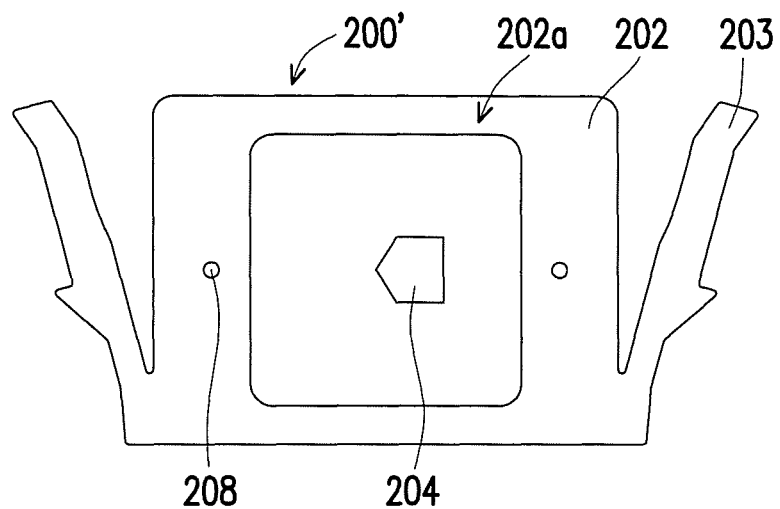
FIG. 1D shows a top view of a collection component of the sample processing kit according to another embodiment of this invention.
Figure 1E:
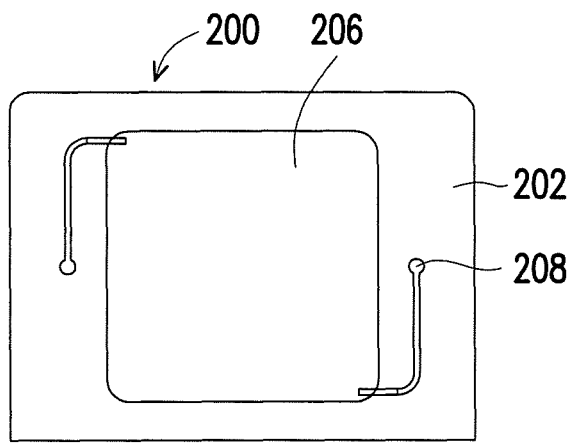
FIG. 1E schematically illustrates a cross-sectional view of the collection component of the sample processing kit according to another embodiment of this invention.

Referring to another embodiment of the collection component as shown in FIGS. 1D-1E, the collection component 200' includes a chip body 202 having an intake opening 204 on the top surface 202a. In addition, the chip body 202 may further includes one or more arm portions 203 at both sides for better fitting into the slot 150. However, such design is optional. As shown in FIG. 1E, the collection chamber 206 is connected with at least one waste outlet 208 (two outlets are shown herein).

The size of the collection component 200 or 200' may be 0.3~5 centimeters for the length or the width as well as a thickness of 0.1~5 centimeters, for example. The loaded volume of the collection chamber 206 may be 10 microliters~5 ml, for example. The collection component 200 or 200' may be fabricated as several slices and then assembled or stacked together. The material of the collection component 200 or 200' may be a plastic material, such as polymethyl methacrylate (PMMA), or other thermoplastics. Preferably, the collection component 200 or 200' may be fabricated as 2~4 slices and then fixed together by waterproof adhesive materials (such as PDMS) or by ultrasonic welding or dispensing or double tape. The collection component 200 or 200' may be opened by removing one or more upper slice(s) of the collection component to expose the collection chamber 206 for easy sample withdrawal. By doing so, once the desired sample is collected within the collection chamber 206 of the collection component 200/200', the other slice(s) is removed and only the slice(s) holding the sample (i.e. the slice containing the collection chamber) is preserved for further experimentation.

Figure 2:
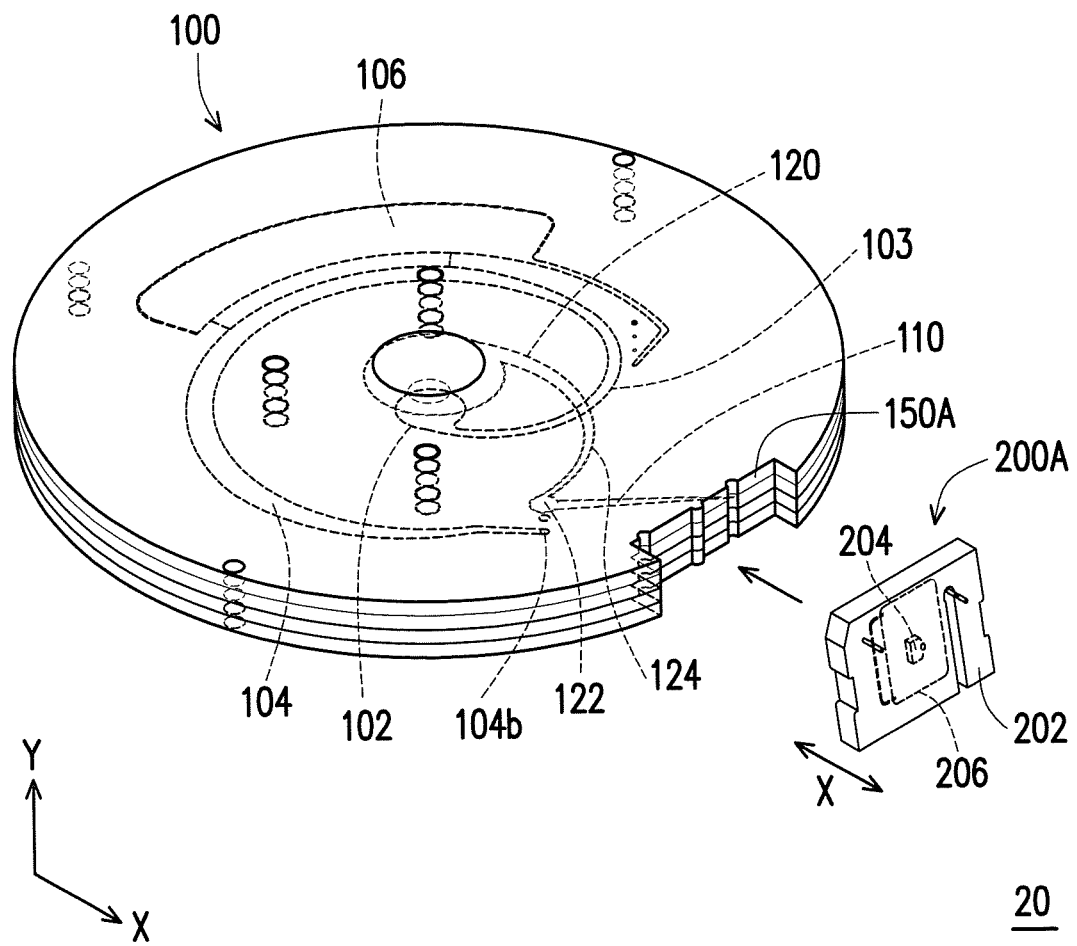
FIG. 2 schematically illustrates a three-dimensional view of a sample processing kit according to another embodiment of this invention.

FIG. 2 schematically illustrates a three-dimensional view of a sample processing kit according to another embodiment of this invention. The sample processing kit 20 includes at least a centrifugal microfluidic disk 100 and a collection component 200. The slot 150A of the microfluidic disk 100 is located at a rim part of the microfluidic disk 100 and the slot 150A opens laterally and directly to the outer environment. The slot 150A is also configured to accommodate the detachable collection component 200A. That is, the shape of the slot 150 should be designed to tightly fit with the collection component 200A. The collection component 200 is removable and detachable and can be laterally inserted into a slot 150A of the centrifugal microfluidic disk 100. After being fitted to the disk, a thickness direction X of the collection component 200 is substantially vertical to a thickness direction Y of the microfluidic disk 100. The centrifugal microfluidic disk 100 and the collection component 200 in this embodiment are similar to the microfluidic disk 100 and the collection component 200 in the previous embodiment, except for the location of the slot and the way of fitting being different. Hence, the details of the microfluidic disk and the collection component may not be further described and will be omitted herein.

Figure 3A:
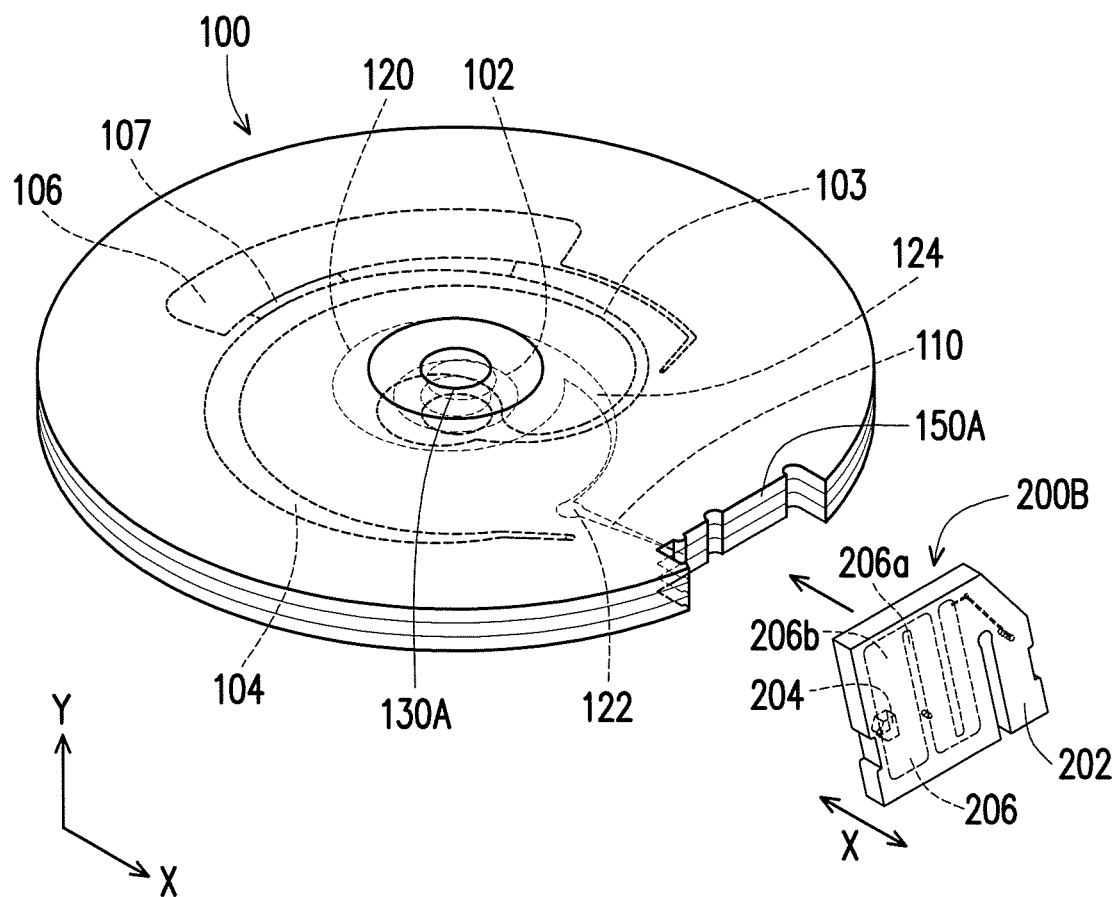
FIG. 3A schematically illustrates a three-dimensional view of a sample processing kit according to another embodiment of this invention.

FIG. 3A schematically illustrates a three-dimensional view of a sample processing kit according to another embodiment of this invention. The sample processing kit 30 includes at least a centrifugal microfluidic disk 100 and a collection component 200B. Different to the centrifugal microfluidic disk 100 of FIG. 1A, the centrifugal microfluidic disk 100 in FIG. 3A includes only one shaft holes 130 located in the center of the sample inlet 102 for accommodating the shaft of spinning.

Figure 3B:
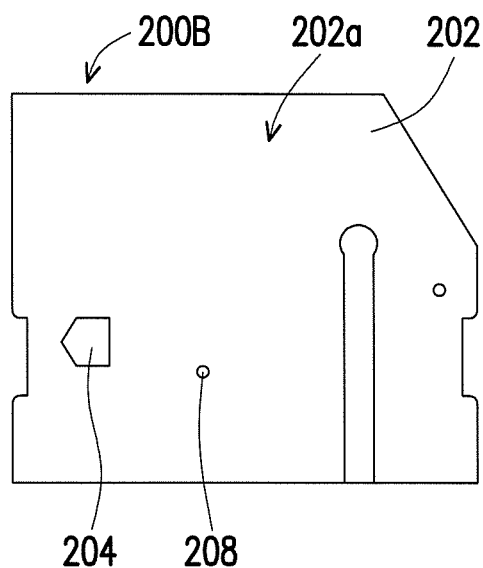
FIG. 3B shows a top view of the collection component of the sample processing kit of FIG. 3A.
Figure 3C:
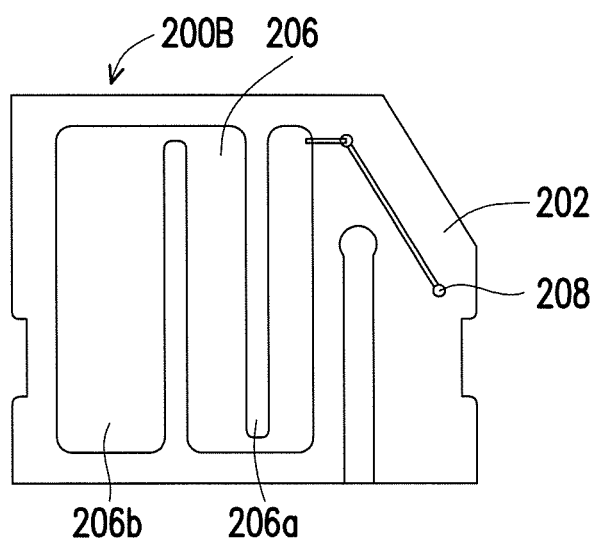
FIG. 3C schematically illustrates a cross-sectional view of the collection component of the sample processing kit of FIG. 3A.

As shown in FIG. 3A, the slot 150A of the microfluidic disk 100 is located at a rim part of the microfluidic disk 100 and the slot 150A opens laterally and directly to the outer environment. The slot 150A is also configured to accommodate the detachable collection component 200B. That is, the shape of the slot 150 should be designed to tightly fit with the collection component 200. The collection component 200 is removable and detachable and can be laterally inserted into a slot 150A of the centrifugal microfluidic disk 100. After being fitted to the disk, a thickness direction X of the collection component 200 is substantially vertical to a thickness direction Y of the microfluidic disk 100. Compared with the previous embodiments, the similar parts or structures of the centrifugal microfluidic disk 100 and the collection component 200B in this embodiment may not be further described and will be omitted herein. FIG. 3B shows a top view of the collection component of the sample processing kit of FIG. 3A, while FIG. 3C schematically illustrates a cross-sectional view of the collection component of the sample processing kit of FIG. 3A. The cross-section of FIG. 3C is taken transversely to the thickness direction of the collection component in FIG. 3A.

Referring to FIGS. 3A-3C, the collection component 200B includes a chip body 202 having an intake opening 204 on the top surface 202a. The intake opening 204 opens into a collection chamber 206 within the chip body 202. As shown in FIGS. 3A & 3C, the collection chamber 206 is divided into several semi-connected portions 206b by a plurality of wall structures 206a. The collection chamber 206 is connected with at least one waste outlet 208 (one outlet is shown herein) so that the extra or needless fluid or running solution is discharged from the waste outlet 208. The intake opening 204 in fact functions as an inlet for receiving the sample flowing from the separation chamber 104 or the reagent via the junction 122 and the conveying channel 110. As shown in FIGS. 3A-3B, the intake opening 204 is located at a peripheral portion of the top surface 202a, rather than located at a central position as shown in FIG. 1B. When the collection component 200B is inserted into the microfluidic disk 100, the intake opening 204 faces toward one side of the slot 150A, so as to receive the fluid.

In the tumor metastatic process, invasive tumor cells in the primary site tend to shed cells into the blood stream, transfer to other organs and grow into new tumors. However, it is very difficult to spot these metastasized cells in the blood stream as these metastasized cells are very scarce when compared to the hematologic cells (about 1 tumour cell per 1 billion cells). It has been noticed that these metastasized cells circulating in the blood stream, i.e. circulating tumour cells (CTCs), may be useful in providing potentially predictive information regarding tumour metastasis and/or efficacy of a particular therapy. For the experimentation purposes, these rare cells, such as CTCs, may be separated and collected from the blood sample.

In the following embodiment, the whole blood is used as an example of the biological sample and the separation and collection of the rare cells from the whole blood may be used for describing the operation of the sample processing kit and the related automation station.

Figure 4A:
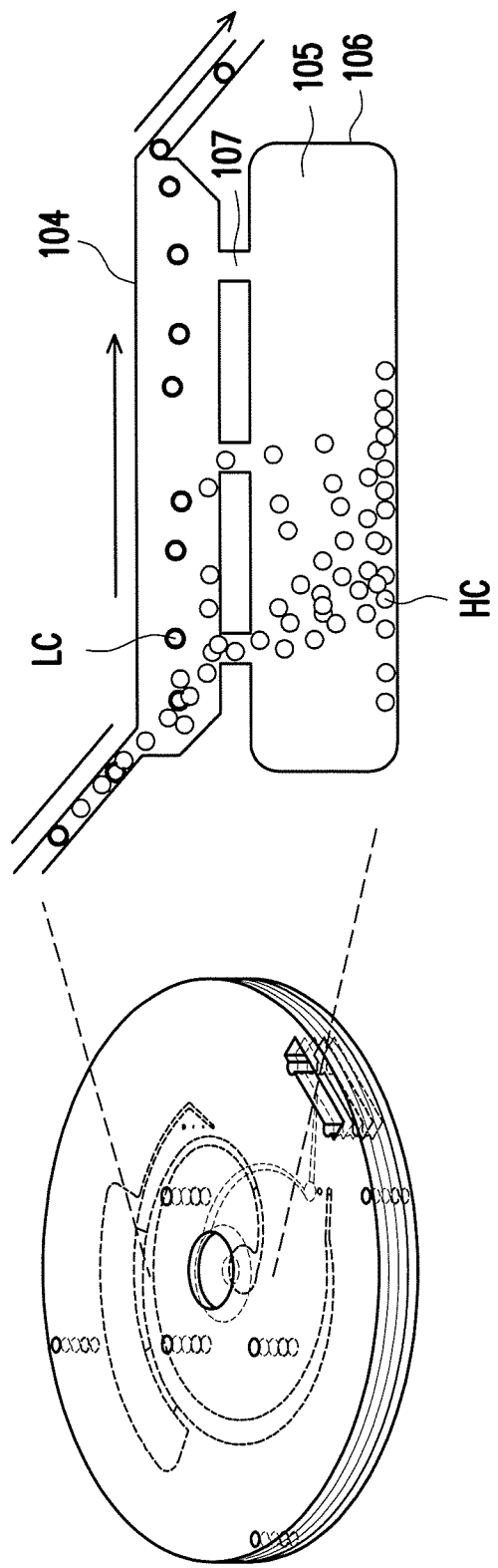
FIG. 4A schematically illustrates a cross-sectional view along the thickness direction of a portion of the centrifugal microfluidic disk in the sample processing kit according to one embodiment of the present invention.

FIG. 4A schematically illustrates a cross-sectional view along the thickness direction of a portion of the centrifugal microfluidic disk in the sample processing kit according to one embodiment of the present invention. FIG. 4A focuses on the portion of the separation chamber and the settling chamber in order to show the principle of cell or molecule separation. The density gradient solution 105 is firstly loaded into the separation chamber 104 and the settling chamber 106 prior to the loading of the sample. The density gradient solution 105 may be a Ficoll-Paque solution (Ficoll-Paque™ plus, GE Healthcare, No. 17-1440-02), for example. During spinning of the disk 100, the centrifugal force drives the fluid (the fluidic sample+the buffer) flowing radially outward from the central sample inlet 102 outward along the spiral-shaped connecting channel 103 and the separation chamber 104 and then outward toward the settling chamber 106 that is arranged closer to the circumferential edge of the disk 100 and surrounding the separation chamber 104. That is, the fluidic sample, such as the blood sample containing light cells LC and heavy cells HC, loaded from the sample inlet flows into the separation chamber 104 (flow direction indicated by the arrow). Through the act of the centrifugal force and the selection of the density gradient solution 105, the light cells LC or light molecules are suspended and flows from the separation chamber 104 further into the collection chamber (flow direction indicated by the arrow), while the heavy cells HC or heavy molecules are settled and washed into the settling chamber 106. The flow path of the sample starts from the sample inlet 102, along the connecting channel 103, the separation chamber 104 and the settling chamber 106 and a portion of the sample (the light cells LC or light molecules) flows into the collection component 200 fitted within the slot 150 via the junction 122 and the conveying channel 110.

By adjusting the flow conditions and/or the density of the density gradient solution 105, the target cells or molecules can be easily isolated from the biological sample and collected by the collection component 200.

As the target cells or molecules are collected in the collection component 200, further treatment(s) may be performed to process the target cells or molecules. For example, the target cells may be further labeled within the collection component 200 before the removal of the collection component 200. In this case, instead of the sample inlet 102, the labeling reagent may be loaded from the reagent inlet 120, pass through the linking channel 124, the junction 122, the conveying channel 110 and flow into the collection component 200 (FIG. 1A). The flow path of the chemical or the labeling reagent starts from the reagent inlet (chemical inlet) 120, through the linking channel 124, the junction 122, the conveying channel 110 and ends at the collection chamber 206 of the collection component 200, without entering the separation chamber or the settling chamber. The chemical may include one or more selected from fluorescent dyes, antibodies, immuno-markers, quantum dots, magnetic beads, labeling materials or sample preparation materials.

Figure 4B:
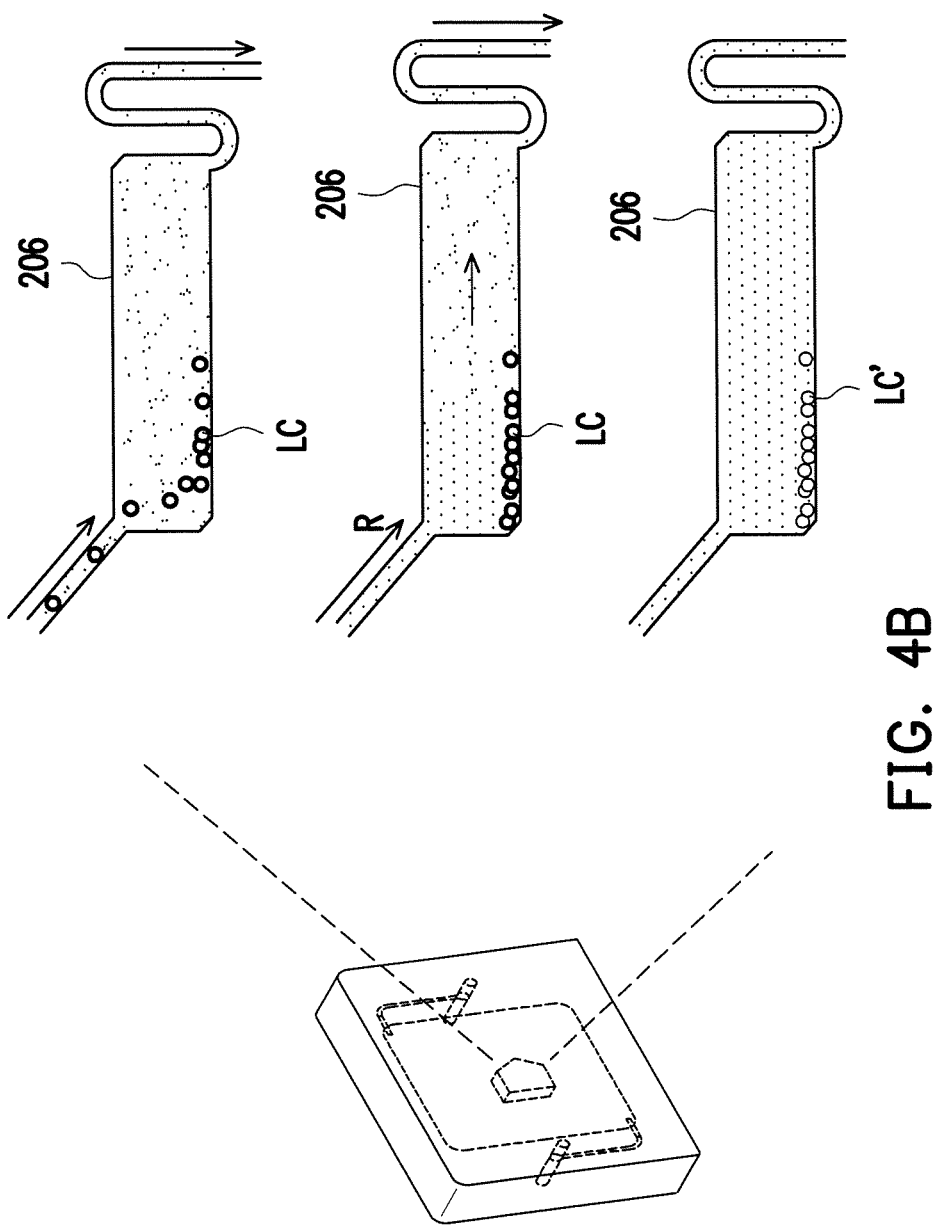
FIG. 4B schematically illustrates a cross-sectional view along the thickness direction of a portion of the collection component in the sample processing kit according to one embodiment of the present invention.

FIG. 4B schematically illustrates a cross-sectional view along the thickness direction of a portion of the collection component in the sample processing kit according to one embodiment of the present invention. FIG. 4B focuses on the portion of the collection chamber in order to show the principle of cell labeling. As shown in the top part of FIG. 4B, light cells LCs are collected in the collection chamber 206 of the collection component 200 (flow direction indicated by the arrow). Later on, the reagent R (i.e. a chemical, such as a fluorescent dye, antibodies, immuno-markers, quantum dots, magnetic beads, or other labeling or sample preparation materials) is loaded into the collection chamber 206 of the collection component 200 and incubated with the light cells LC (shown in the middle part of FIG. 4B) and then the labeled light cells LC' are obtained after incubation (shown in the bottom part of FIG. 4B). Finally, the washing buffer is injected to wash out the unreacted labeling reagent.

The labeling process may be any available labeling process, such as immuno-labeling, fluorescence labeling or magnetic bead labeling.

In this embodiment, the labeling process is simply performed once, but if necessary, several times of labeling (i.e. multiple labeling or multi-marker labeling) may be performed to the target(s) collected in the collection chamber.

Figure 5A:
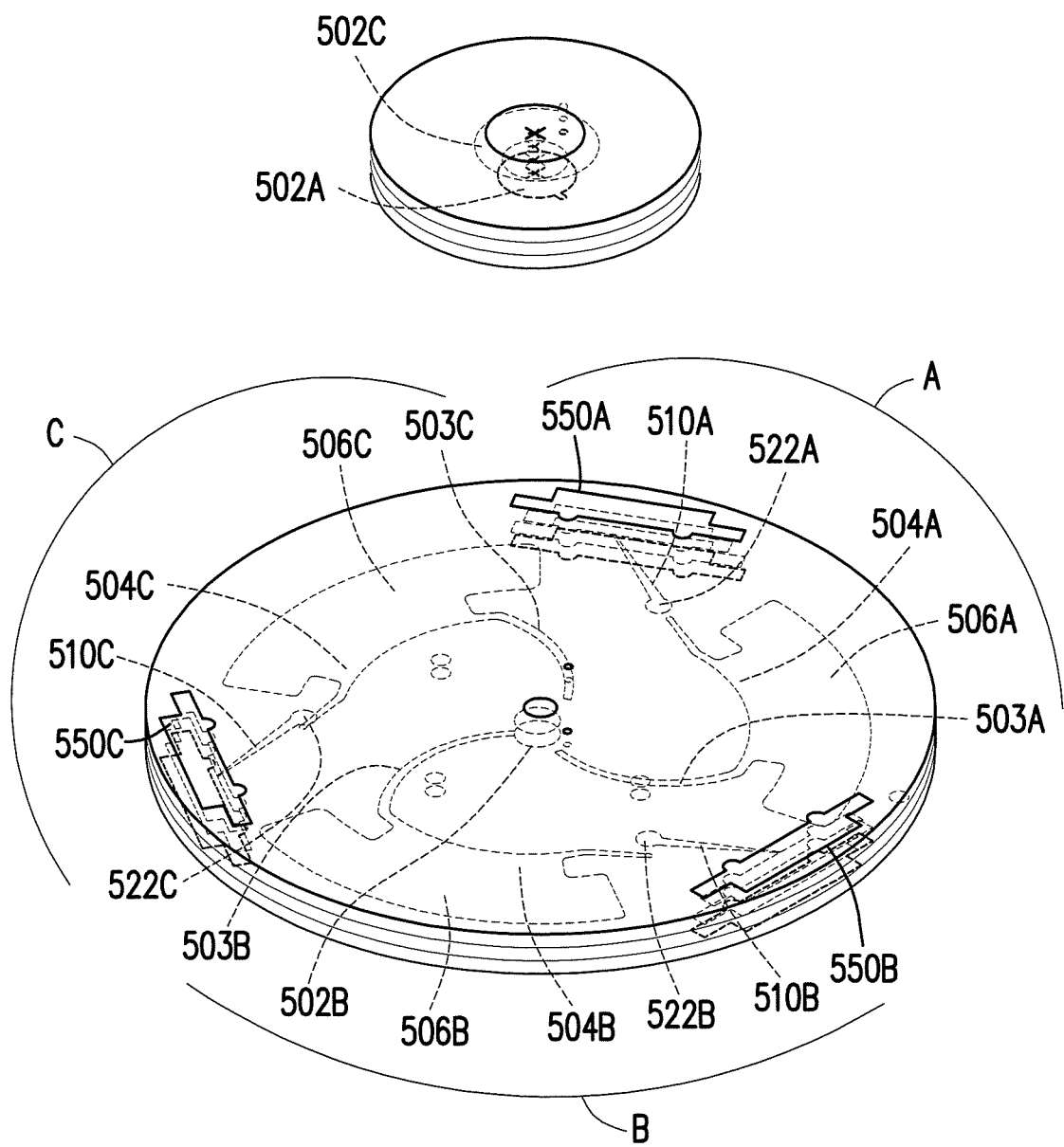
FIG. 5A schematically illustrates a three-dimensional view of a centrifugal microfluidic disk according to one embodiment of this invention.
Figure 5B:
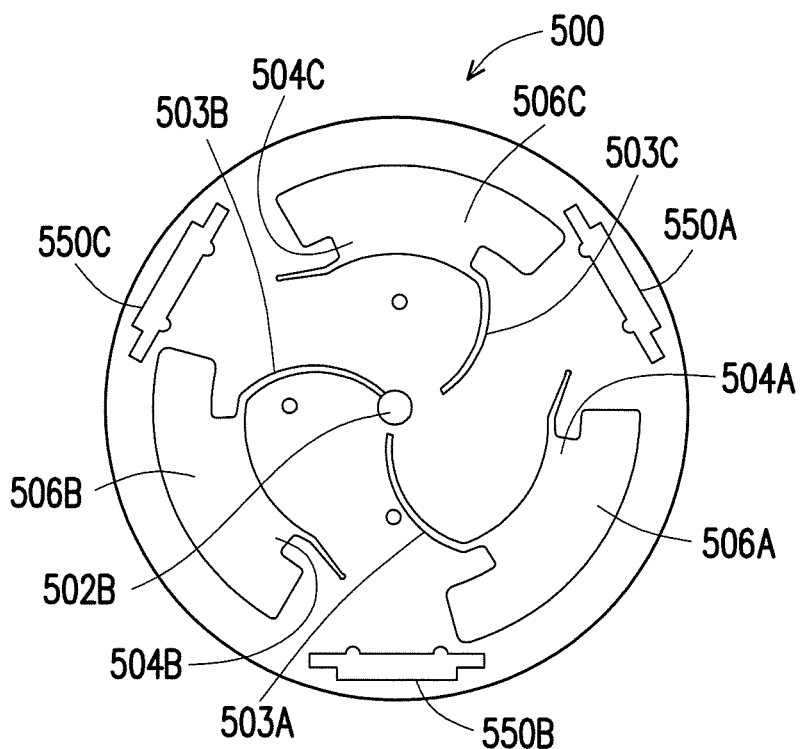
FIGS. 5B-5E schematically illustrate various cross-sectional views of the centrifugal microfluidic disk of FIG. 5A.
Figure 5C:
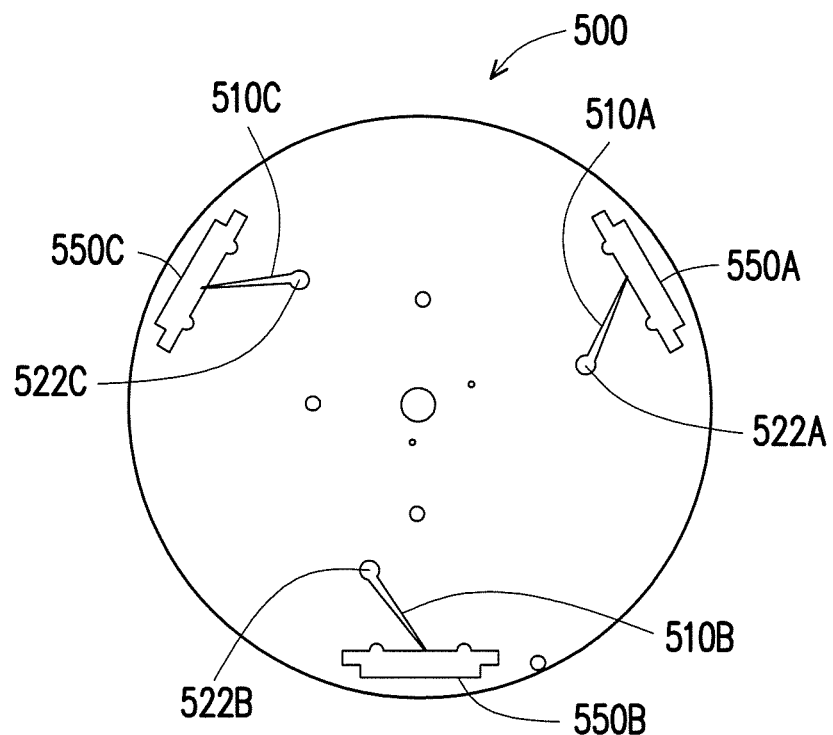
Figure 5D:
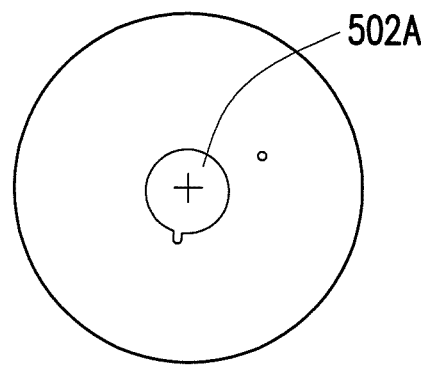
Figure 5E:
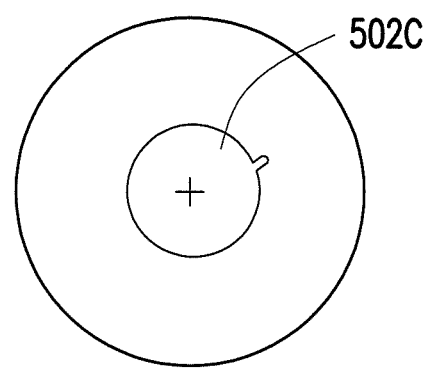

FIG. 5A schematically illustrates a three-dimensional view of a centrifugal microfluidic disk according to one embodiment of this invention. FIGS. 5B-5E schematically illustrate various cross-sectional views of the centrifugal microfluidic disk of FIG. 5A. FIGS. 5B-5E show cross-sections sequentially from lower levels to upper levels of the disk of FIG. 5A. The cross-sections of FIGS. 5B-5E are taken transversely to the thickness direction of the disk of FIG. 5A. The centrifugal microfluidic disk 500 may be a round or elliptical disk and the microfluidic disk 500 in FIG. 5A may be fabricated as several slices and then assembled or stacked together. In FIG. 5A, the stacked slices of the disk 500 are shown as two separate portions (one lower larger portion and one upper smaller portion) for description purpose. The material of the microfluidic disk 500 may be a plastic material, such as polymethyl methacrylate (PMMA), or other thermoplastics. The diameter of the microfluidic disk 500 may ranges from 6 to 18 centimeters, preferably 12~14 centimeters, for example.

The centrifugal microfluidic disk 500 in FIG. 5A in fact includes three individual processing sections A, B, C, and each processing section can be considered as a centrifugal microfluidic component that functions similarly as the aforementioned microfluidic disk 100. In principle, the centrifugal microfluidic disk 500 integrate at least three independently functioning microfluidic components as one microfluidic disk. Along with three separate collection components as described above, three individual sample processing kits are integrated as one sample processing kit, so that the processing procedures of these three individual sample processing kits (with the same or different samples) can be performed at the same time by one single centrifugal process. Such design is very cost-economic and offers high efficiency and high yield.

As shown in FIGS. 5A-5E, each processing section A, B or C (A/B/C) of the centrifugal microfluidic disk 500 include a sample inlet 502A/502B/502C, a connecting channel 503A/503B/503C, a separation chamber 504A/504B/504C and a settling chamber 506A/506B/506C. The sample inlet 502A/502B/502C is located on a central position of the disk 500 and the same or different sample may be loaded into different processing sections of the disk 100 through the sample inlet 502A/502B/502C. The separation chamber 504A/504B/504C is connected with the sample inlet 502A/502B/502C through the corresponding connecting channel 503A/503B/503C. The sample inlets 502A/502B/502C are of different sizes and located at different levels and arranged in a concentric way. The settling chamber 506A/506B/506C is connected with the separation chamber 504A/504B/504C, and during the centrifugal process, the to-be-collected target(s) or cell(s) in the injected fluid sample can flow into the separation chamber 504A/504B/504C, while the non-collected portion of the fluid sample flows into the settling chamber 506A/506B/506C. By adjusting the flow conditions and/or the density of the density gradient solution, the target(s) or cell(s) can be easily isolated from the biological fluidic sample and flows into the collection component(s).

One end of the separation chamber 504A/504B/504C is physically connected to a junction 522A/522B/522C. The to-be-collected target(s) or cell(s) flowing through the separation chamber 504A/504B/504C, via the junction 522A/522B/522C, further flows into a conveying channel 510A/510B/510C that is connected to the slot 550A/550B/550C. The junction 522A/522B/522C extends vertically (across two levels) and communicates the separation chamber 504A/504B/504C located at the lower level with the conveying channel 510A/510B/510C located at the upper level. That is, the separated sample from the end of the separation chamber 504A/504B/504C flows through the junction 522A/522B/522C and the conveying channel 510A/510B/510C and then flows into the transverse slot 550A/550B/550C (i.e. collected by the collection component fitted therein). As described above, the collection component 200 (FIG. 1A) may be removed from the slot of the disk after the separated sample has been collected in the later stage.

Figure 6A:
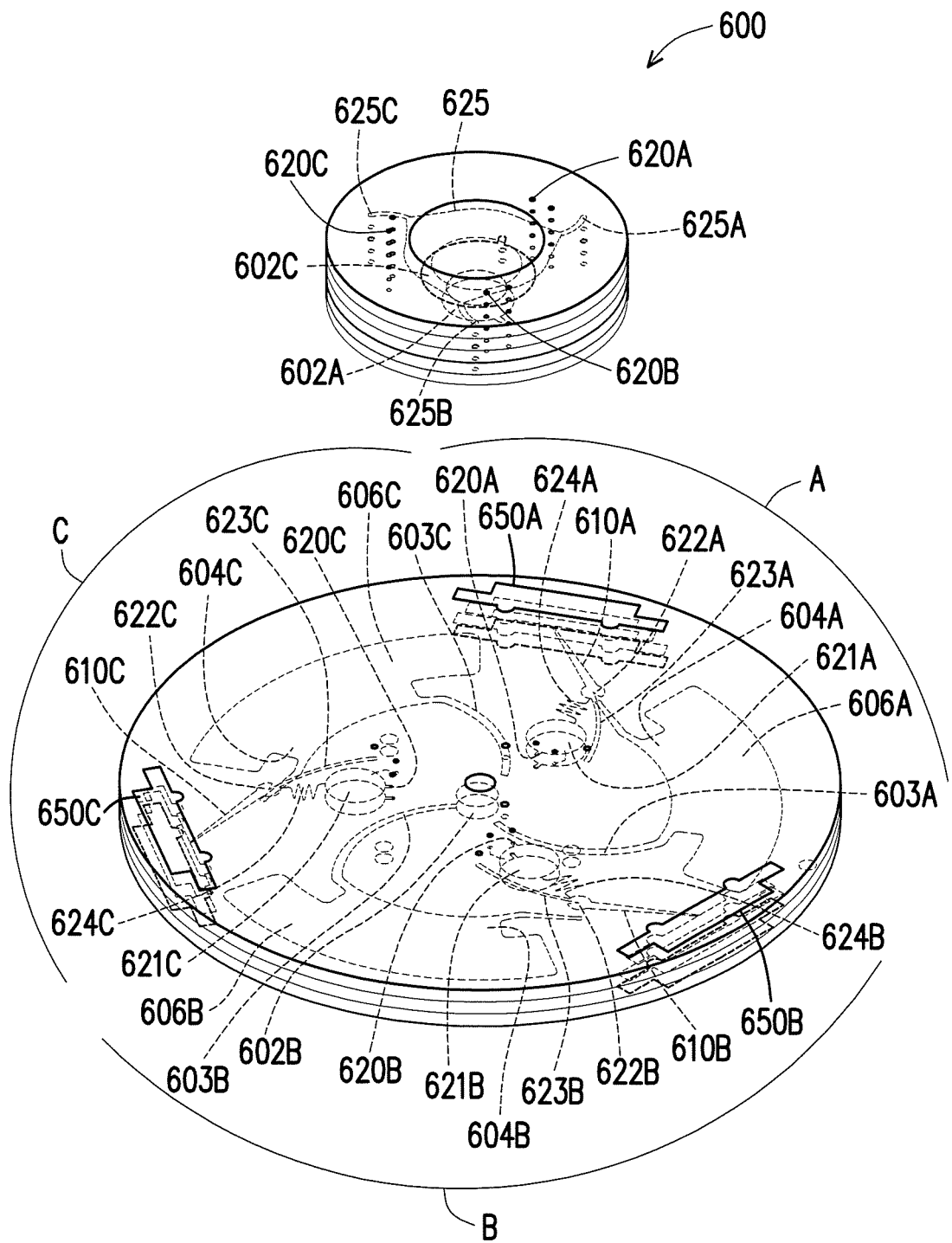
FIG. 6A schematically illustrates a three-dimensional view of a centrifugal microfluidic disk according to another embodiment of this invention.

FIG. 6A schematically illustrates a three-dimensional view of a centrifugal microfluidic disk according to another embodiment of this invention. FIGS. 6B-6G schematically illustrate various cross-sectional views of the centrifugal microfluidic disk of FIG. 6A. FIGS. 6B-6G show cross-sections sequentially from lower levels to upper levels of the disk of FIG. 6A. The cross-sections of FIGS. 6B-6G are taken transversely to the thickness direction of the disk of FIG. 6A. The centrifugal microfluidic disk 600 may be a round or elliptical disk and the microfluidic disk 600 may be fabricated as several slices and then assembled or stacked together. In FIG. 6A, the stacked slices of the disk 600 are shown as two separate portions (one lower larger portion and one upper smaller portion) for description purpose.

The centrifugal microfluidic disk 600 in FIG. 6A in fact is divided into three individual processing sections A, B, C, and each processing section can function similarly as the aforementioned microfluidic disk 100. Similarly, the design of the centrifugal microfluidic disk 600 integrates at least three independently functioning microfluidic disks as one microfluidic disk and the microfluidic disk 600 can be fitted with three collection components as described above to function as three individual sample processing kits during one single centrifugal process. The design of the centrifugal microfluidic disk 600 is similar to the design of the microfluidic disk 500, except for additional flow path design for loading reagent(s) or dye(s).

Figure 6B:
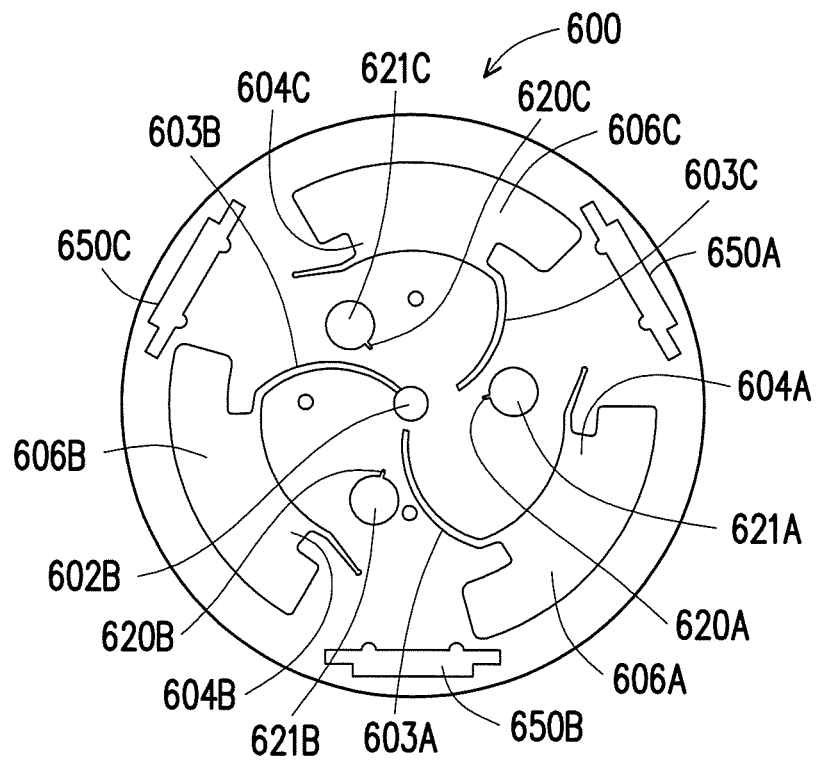
FIGS. 6B-6G schematically illustrate various cross-sectional views of the centrifugal microfluidic disk of FIG. 6A.

As shown in FIGS. 6A-6G, each processing section A, B or C (A/B/C) of the centrifugal microfluidic disk 600 include a sample inlet 602A/602B/602C, a connecting channel 603A/603B/603C, a separation chamber 604A/604B/604C and a settling chamber 606A/606B/606C. The sample inlet 602A/602B/602C is located on a central position of the disk 600 and the same or different sample may be loaded into different processing sections of the disk 100 through the sample inlet 602A/602B/602C. The separation chamber 604A/604B/604C is connected with the sample inlet 602A/602B/602C through the corresponding connecting channel 603A/603B/603C. The sample inlets 602A/602B/602C are of different sizes and located at different levels and arranged in a concentric way. In FIG. 6B, a reservoir 621A/621B/621C is arranged beside the connecting channel 603A/603B/603C in the respective processing section, and a reagent inlet 620A/620B/620C is connected to the reservoir 621A/621B/621C. The settling chamber 606A/606B/606C is connected with the separation chamber 604A/604B/604C, and during the centrifugal process, the to-be-collected target(s) or cell(s) in the injected fluid sample can flow into the separation chamber 604A/604B/604C, while the non-collected portion of the fluid sample flows into the settling chamber 606A/606B/606C. One end of the separation chamber 604A/604B/604C is physically connected to a junction 622A/622B/622C. The to-be-collected target(s) or cell(s) flowing through the separation chamber 604A/604B/604C, via the junction 622A/622B/622C, further flows into a conveying channel 610A/610B/610C that is connected to the slot 650A/650B/650C. The junction 622A/622B/622C extends vertically (across two levels) and communicates the separation chamber 604A/604B/604C located at the lower level with the conveying channel 610A/610B/610C located at the upper level. That is, the separated sample from the end of the separation chamber 604A/604B/604C flows through the junction 622A/622B/622C and the conveying channel 610A/610B/610C and then flows into the transverse slot 650A/650B/650C (i.e. collected by the collection component fitted therein). As described above, the collection component 200 (FIG. 1A) may be removed from the slot of the disk after the separated sample has been collected in the later stage.

Figure 6C:
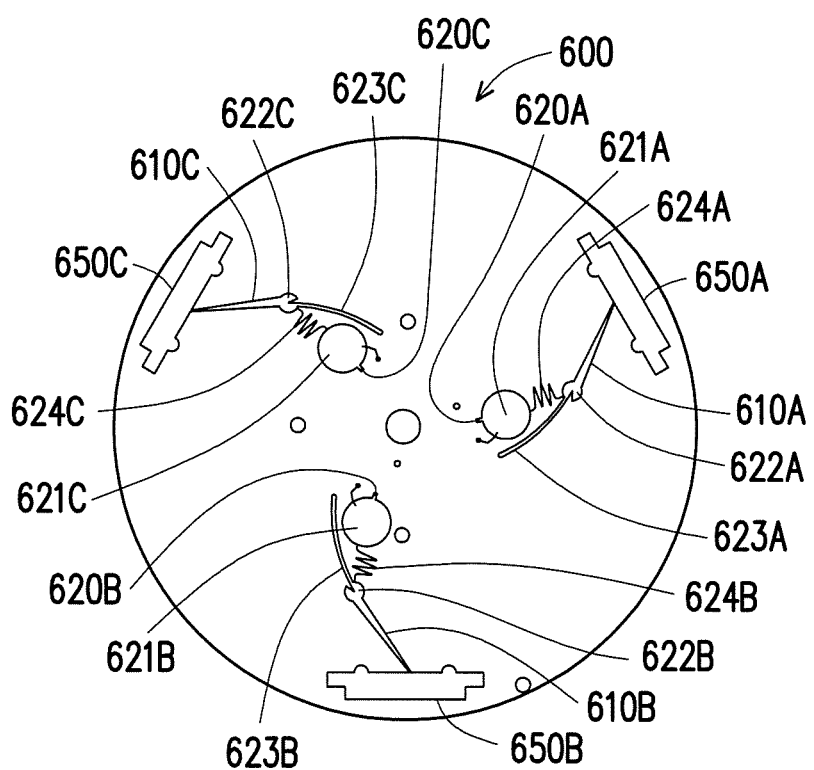
Figure 6D:
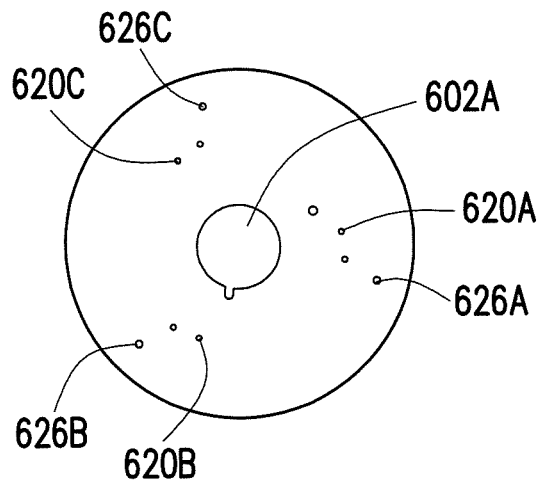
Figure 6E:
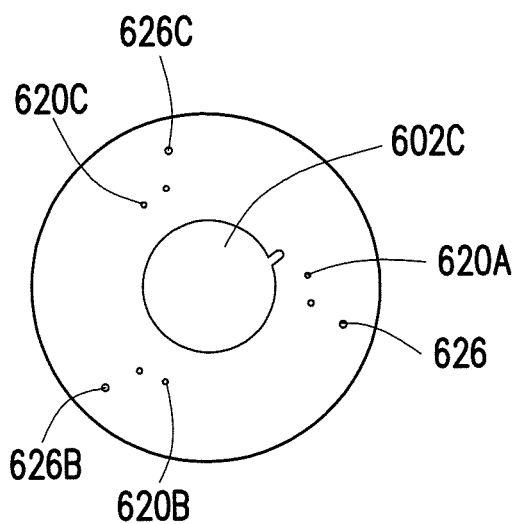
Figure 6F:
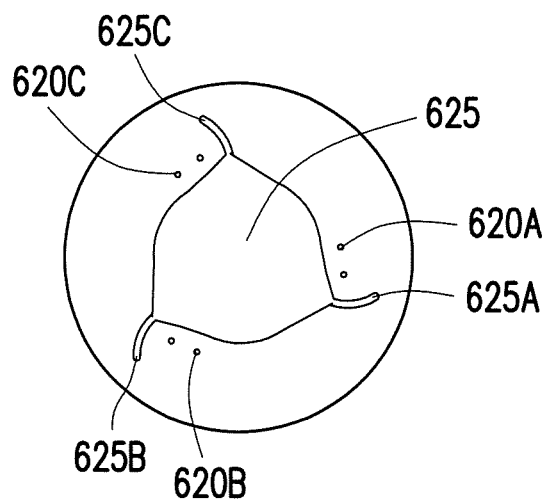
Figure 6G:
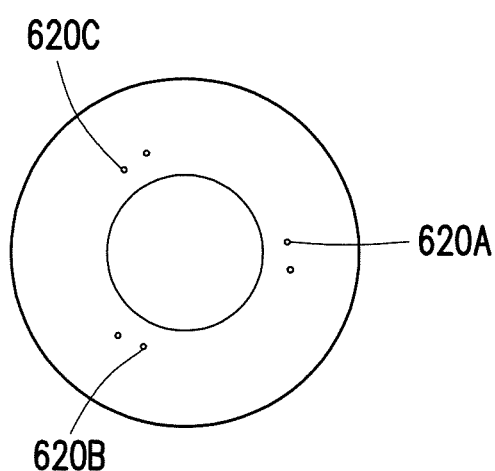

In FIGS. 6A & 6C, in addition to the reagent inlet 620A/620B/620C and the reservoir 621A/621B/621C connected to the reagent inlet 620A/620B/620C, each processing section A, B or C of the disk 600 also includes a linking channel 624A/624B/624C connecting the reservoir 621A/621B/621C and the junction 622A/622B/622C and a washing channel 623A/623B/623C connected to the junction 622A/622B/622C. The washing buffer loaded from a washing inlet 625 (located at an upper level) is received by the washing channel 623A/623B/623C and flows into the conveying channel 610A/610B/610C (via the junction 622A/622B/622C) to dilute the sample or wash off the remains. In FIG. 6F, it is shown that the washing inlet 625 is a substantively triangular opening (with three ends 625A/625B/625C) located at the second topmost level of the disk 600 and is open to the outer environment by partial exposure through the central opening at the topmost level (FIG. 6G) of the disk 600. The ends 625A/625B/625C of the washing inlet 625 are respectively connected with the washing channel 623A/623B/623C located at a much lower level (FIG. 6C) through joints 626A/626B/626C penetrating through different levels. The washing inlet 625 and the sample inlets 602A/602B/602C are openings located at different levels and of different sizes, but are arranged in a concentric way.

The same or different reaction reagent(s) may be loaded into the reservoir 621A/621B/621C of the disk 600 via the reagent inlet 620A/620B/620C independently and the reservoir 621A/621B/621C extends across two levels (as shown in FIGS. 6B-6C) as to hold the loaded reagent(s) therein. The reagent inlet 620A/620B/620C extends through all the above levels and is open to the outer environment so that the reagent(s) can be loaded from the topmost level of the disk 600.

The flow path of the sample starts from the sample inlet 602A/602B/602C, along the connecting channel 603A/603B/603C, the separation chamber 604A/604B/604C and a portion of the sample (to-be-collected targets or cells) ends at the collection chamber 206 of the collection component 200 that is fitted within the slot 650A/650B/650C. As the target(s) or cell(s) are collected in the collection chamber 206 of the collection component, further treatment(s) may be performed to process the target(s) or cells by injecting the reagent(s) into the disk 600. For example, the target cells may be further labeled within the collection chamber by loading the labeling reagent from the reagent inlet 620A/620B/620C, passing through the linking channel 624A/624B/624C, the junction 622A/622B/622C, the conveying channel 610A/610B/610C and flow into the collection chamber of the collection component. The flow path of the reagent starts from the reagent inlet 620A/620B/620C, through the linking channel 624A/624B/624C, the junction 622A/622B/622C, the conveying channel 610A/610B/610C and ends at the collection chamber of the collection component that is fitted within the slot 650A/650B/650C, without entering the separation chamber.

Figure 7:
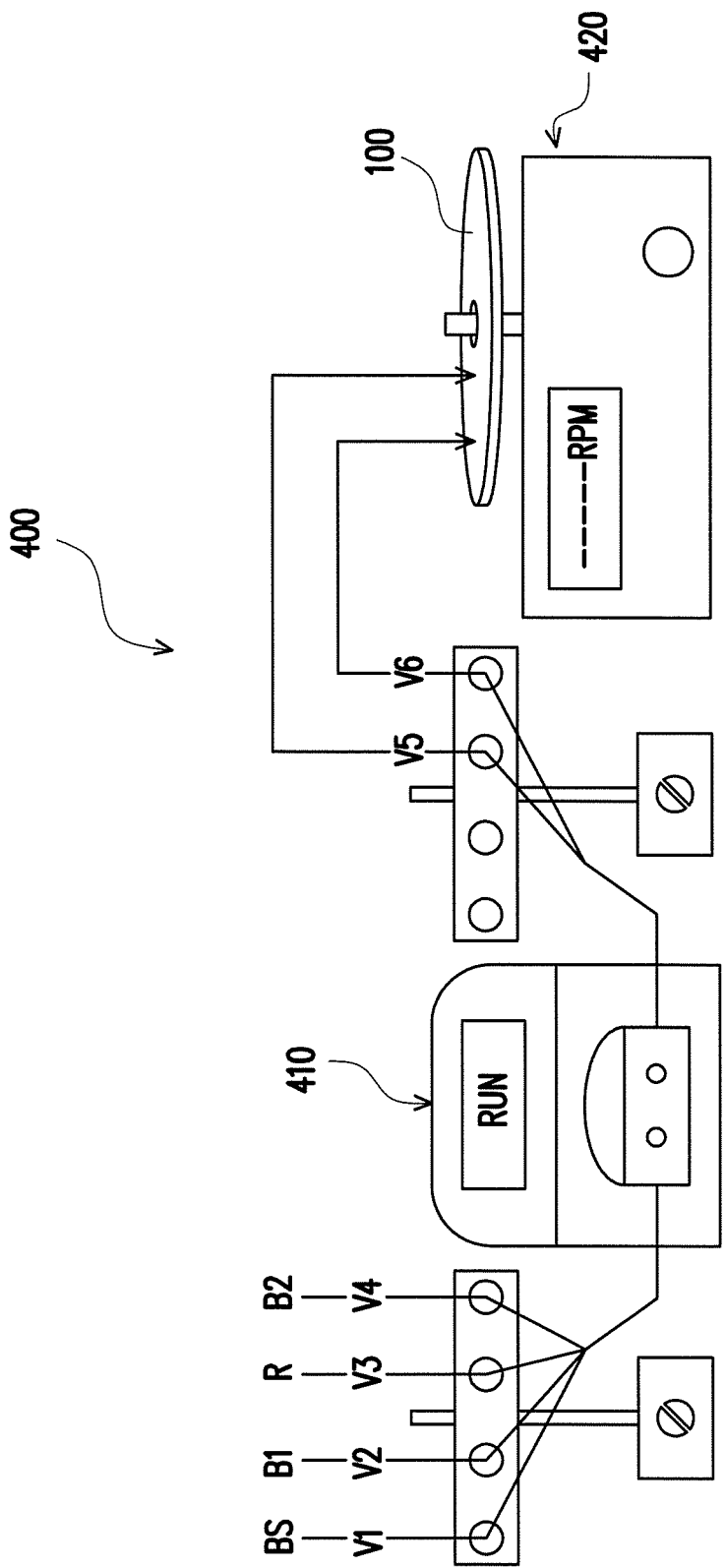
FIG. 7 schematically illustrates an automated workstation according to an embodiment of the present invention.

The sample processing kit according to embodiments of the present invention may be obtained by assembling the above mentioned microfluidic disk 100, 500 or 600 freely with the above mentioned collection component 200, 200A or 200B. The sample processing kit according to embodiments of the present invention may operate together with an automated workstation. FIG. 7 schematically illustrates an automated workstation according to an embodiment of the present invention. The automated workstation 400 includes at least a peristaltic pump 410, a rotation platform 420 and pinch valves V1-V6. The external peristaltic pump 420 can drives the fluid or the buffer solution to provide a stable flow rate for the blood sample. The pinch valves V1-V6 allow fast fluid handling and shut-off so that the entire workstation can be easily programmable. The rotation platform 420 may be powered by a motor so as to spin the sample processing kit (the microfluidic disk and the collection component) at a high speed for high throughput handing. The automated workstation 400 adopts continuous fluidic input, continually pumping the fluidic sample (such as the blood sample) and the buffer by the peristaltic pump and injecting the blood sample continuously during the disk operation. The flow mechanism of the automated workstation 400 is shown in FIG. 7 and the flow direction is marked by the arrow. For example, the pinch valves V1-V4 control the loading (input) of the blood sample, the first buffer, the reagent solution and the second buffer respectively. Driving by the pump 420, the blood sample is injected into the inner sample inlet by unlocking the pinch valve V2 and V5. Also, driving by the pump 420, the reagent solution is injected into the outer reagent inlet by unlocking the pinch valve V4 and V6. The reagent solution may include one or more types of fluorescent dyes, antibodies, immuno-markers, or even labeled magnetic beads.

According to the automated centrifugal system disclosed in this embodiment, continuous-flow microfluidic operation can be achieved, which provides significant advantages, including large sample volumes (up to 20 ml), simple implementation and less pollution. As described previously, the relative locations of the sample inlet and the reagent inlet can be arranged in a concentric way or in an eccentric way, and the centrifugal disk may be spun with a rotating shaft located at the center part of the disk or without a main shaft of rotation.

The processing steps of the fluidic sample (such as the blood sample containing light cells and heavy cells) in the automated workstation may be summarized as: introducing the blood sample into the microfluidic disk within the automated workstation; spinning the sample processing kit (the microfluidic disk and the collection component) by the rotation platform to drive the blood sample flowing radially outward into the separation chamber, wherein the light cells of the blood sample flow into the collection chamber of the collection component, while the heavy cells are deposited in the settling chamber of the microfluidic disk; and collecting the light cells from the collection chamber by removing the collection component from the microfluidic disk for further experimentation or observation. The operation details may be exemplified as the following steps:

a) fill the blood sample, Ficoll-Paque™ plus solution, the buffers and the reagent solution into the storage tubes.

b) spin the sample processing kit (microfluidic disk 100, 500 or 600 and the collection component 200, 200', 200A or 200B) at 2000~5000 rpm (revolution per minute).

c) during spinning, load and pump Ficoll-Paque™ plus solution from the sample inlet into the disk with a flow rate 50~5000 microliters/minute.

d) from the washing inlet, load and pump PBS/buffer into the disk with a flow rate 50~5000 microliters/minute.

e) load and pump the blood sample (mixed with the buffer) into the disk with a flow rate 50~5000 microliters/minute.

f) from the washing inlet, load and pump PBS/buffer into the disk with a flow rate 50~5000 microliters/minute.

g) from the reagent inlet, load and pump 20~1000 microliters of the reagent solution into the disk with a flow rate 50~3000 microliters/minute.

h) spin the sample processing kit (microfluidic disk and the collection component) at 0~500 rpm for 10~60 minutes used for incubation.

i) spin the sample processing kit (microfluidic disk and the collection component) at 1000~5000 rpm.

j) from the washing inlet, load and pump PBS/buffer into the disk with a flow rate 50~5000 microliters/minute.

k) stop spinning and take the collection component out from the microfluidic disk for observation or further experimentation. The collected cells in the collection chamber may be directly observed or drawn out for other tests or assays.

To characterize the performance of the disk platform, several cancer cell lines were used in the experiments to represent the target cells. These cell lines are breast cancer cell lines MCF7 and MDA-MB-231, prostate cancer cell line PC3, hepatoma cell lines HEP3B, PLC5 and colorectal cancer cell line Colo205. The blood samples were collected from healthy human volunteers and about 100~200 cancer cells were mixed into 2 ml of the whole blood to simulate the real cases with rare cells.

Figure 8:
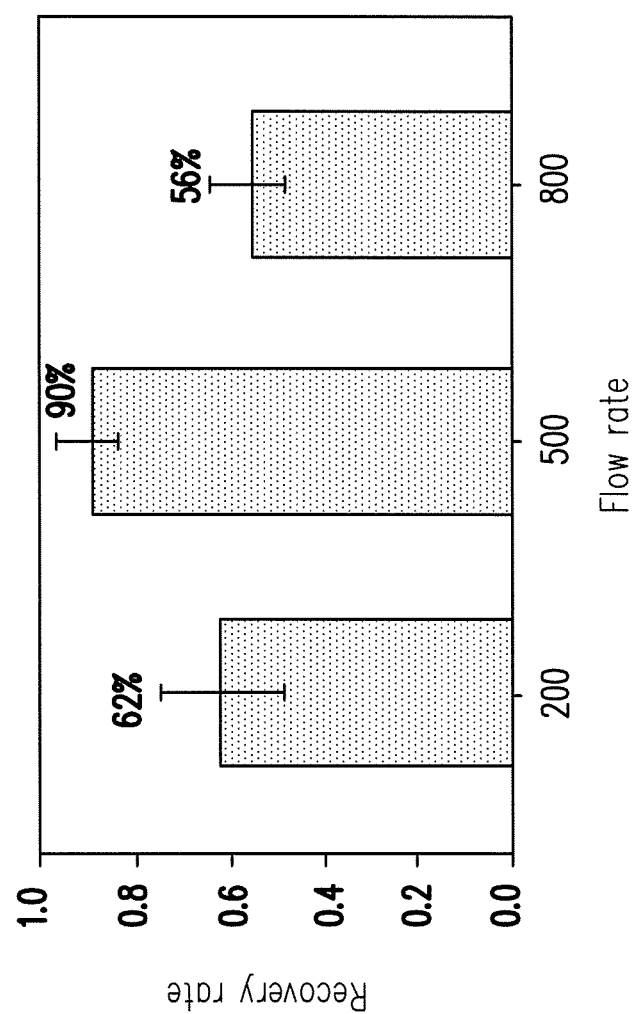
FIG. 8 shows the relationship between flow rate and the recovery ratio of cell line MCF7.
Figure 9:
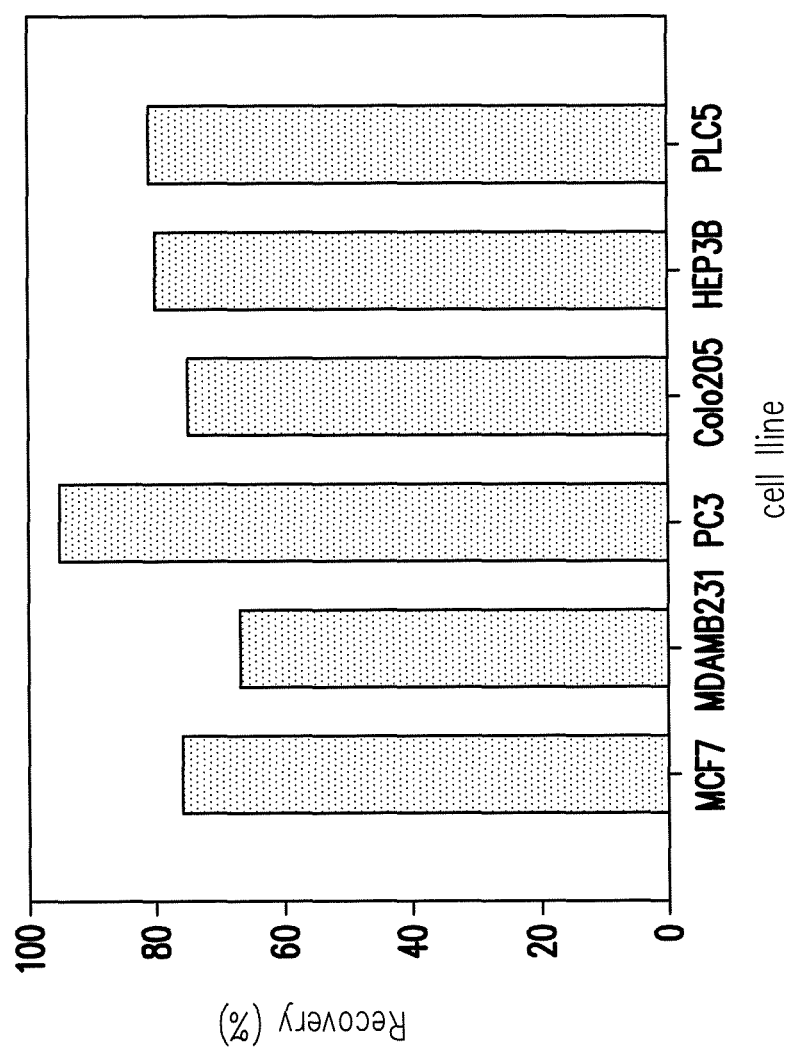
FIG. 9 shows the recovery ratios of different types of cell lines.

For determining the optimal flow rate of this disk platform, we prepared the sample for the experiments by using spiked MCF7 that was labeled with anti-EpCAM-PE and mixing with 1 ml of blood. FIG. 8 shows the relationship between flow rate and the recovery ratio of the cell line MCF7 for the disk platform using the microfluidic disk 100. The result indicated that the optimal flow rate in the present experiment is 500 microliters/minute and the recovery ratio (i.e. the harvest amount) is around 0.9 (90% in percentage). Using the flow rate of 500 microliters/min for further experiments, different types of cancer cell lines were tested. FIG. 9 shows the recovery ratios of different types of cell lines. The recovery ratios of different types of cancer cell lines with the disk platform using the microfluidic disk 100 range from 60°~90%, generally above 70%. Comparable results are observed for the disk platform using the microfluidic disk 500 or 600, as the recovery ratios of the cell line MCF7 are approximately 70%. These results demonstrated that the sample processing kit (microfluidic disk and the collection component) can efficiently separate and specifically collect cells (i.e. rare cells) of a very small amount from the whole blood. Specifically, the recovery rate for the cell lines are respectively: more than 90% for the prostate cancer cell line PC3, about 80% for the hepatoma cell lines HEP3B, PLC5, and about 70~80% for the breast cancer cell lines with MCF7 and the colorectal cancer cell line Colo205, as well as about 60~70% for the breast cancer cell lines MDA-MB-231.

In addition, the labeling effects of the labeling reagent loaded into the collection component for labeling the collected cell(s) have been tested and satisfactory labeling effects are observed for the cell lines using the microfluidic disk 100, 500 or 600.

Compared with prior microfluidic devices that may isolate specific cells from the blood through immunoaffinity separation, the cell line (e.g. MDA-MB-231) with relatively low antigen expression level was captured efficiently. This indicates that the sample processing kit using density gradient separation as disclosed in the previous embodiments can efficiently isolate the target cells independent of the expression level of the tumor cells marker(s).

Because the sample processing kit includes the collection component to collect the sample in situ during the centrifugation and the collected sample hold within the collection component needs not to be removed or drawn out from the collection component for further treatment, there is no concerns regarding sample contamination or sample loss. This significantly enhances the workability of rare sample(s) or sample(s) of very low amounts.

This advanced sample processing kit have many potential applications in biological, biochemical and medicinal fields. The sample processing kit is compatible with fully automated sample preparation and is able to hold flexible sample volumes (ranging from 0.1 ml to 20 ml). The sample processing kit can achieve high recovery rates up to 60%~90% for scarce samples. Further, the sample processing kit using the microfluidic disk in fact integrates continuous density gradient separation and multi-marker labeling.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily being drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to faun an equivalent method without departing from the teachings of the invention.

What is claimed is:

1. A sample processing kit, comprising at least one centrifugal microfluidic component and at least one collection component, wherein the at least one centrifugal microfluidic component comprises:
    a sample inlet for loading a biological sample into the centrifugal microfluidic component;
    a separation chamber, connected with the sample inlet; and
    a settling chamber, wherein the settling chamber is connected with the separation chamber through a connecting portion and is arranged radially outward from the separation chamber, an extension of the connecting portion from the separation chamber to the settling chamber fully follows a radially outward direction, and the separation chamber, the connecting portion and the settling chamber form one continuous cavity without a valve therein; and
    a fitting site for accommodating the at least one collection component, and
    wherein the at least one collection component and the at least one centrifugal microfluidic component are separate components and when the at least one collection component is detachably fitted into the fitting site of the at least one centrifugal microfluidic component, the at least one collection component is connected with the separation chamber of the at least one centrifugal microfluidic component, the at least one collection component has an intake opening thereon for receiving the biological sample that is processed by the at least one centrifugal microfluidic component, and the at least one collection component is disconnected from the fitting site of the at least one centrifugal microfluidic component after receiving the processed biological sample.

2. The sample processing kit of claim 1, wherein the collection component comprises a chip body with the intake opening thereon and a collection chamber therein, and the intake opening opens into the collection chamber so that the biological sample that is processed by the at least one centrifugal microfluidic component flows into the collection chamber.

3. The sample processing kit of claim 2, wherein a flow path of the biological sample starts from the sample inlet, substantially along the separation chamber and ends at the collection chamber of the at least one collection component.

4. The sample processing kit of claim 2, wherein the at least one centrifugal microfluidic component further comprises a reagent inlet for loading a reagent, a reservoir for receiving the reagent loaded from the reagent inlet and a linking channel connecting the reservoir and the at least one collection component.

5. The sample processing kit of claim 4, wherein a flow path of the reagent starts from the reagent inlet, through the reservoir and the linking channel and ends at the collection chamber of the at least one collection component.

6. The sample processing kit of claim 1, wherein the at least one centrifugal microfluidic component further comprises a reagent inlet for loading a reagent and a linking channel connecting the reagent inlet and the at least one collection component.

7. The sample processing kit of claim 6, wherein a flow path of the reagent starts from the reagent inlet, through the linking channel and ends at the collection chamber of the at least one collection component.

8. The sample processing kit of claim 1, wherein the sample processing kit comprises a plurality of centrifugal microfluidic components and a plurality of collection components respectively fitted into the fitting sites of the centrifugal microfluidic components.

9. The sample processing kit of claim 1, wherein the at least one centrifugal microfluidic component further comprises a washing inlet for loading a buffer and a washing channel connecting the washing inlet and the at least one collection component, and the washing inlet and the sample inlet are located at different levels of the at least one centrifugal microfluidic component.

10. The sample processing kit of claim 1, wherein the fitting site is located radially outward from the sample inlet and at a peripheral portion of the at least one centrifugal microfluidic component and the at least one collection component fits into the fitting site.

11. The sample processing kit of claim 10, wherein a thickness direction of the at least one collection component fitted into the fitting site is substantially perpendicular to a thickness direction of the at least one centrifugal microfluidic component.

12. The sample processing kit of claim 1, wherein the fitting site is located radially outward from the sample inlet and at a rim part of the at least one centrifugal microfluidic component and the at least one collection component fits into the fitting site.

13. The sample processing kit of claim 12, wherein a thickness direction of the at least one collection component fitted into the fitting site is substantially perpendicular to a thickness direction of the at least one centrifugal microfluidic component.

* * * * *